(12) United States Patent
Karasawa (10) Patent No.: US 7,496,259 B2
(45) Date of Patent: Feb. 24, 2009

(54) ENDOSCOPE WITH OPTICAL FIBER AND FIBER OPTICS SYSTEM

(75) Inventor: Satoshi Karasawa, Saitama (JP)

(73) Assignees: University of Washington, Seattle, WA (US); Hoya Corporation, Tokyo (JP)

( * ) Notice: Subject to any disclaimer, the term of this patent is extended or adjusted under 35 U.S.C. 154(b) by 0 days.

(21) Appl. No.: 11/619,003

(22) Filed: Jan. 2, 2007

(65) Prior Publication Data
US 2008/0161648 A1    Jul. 3, 2008

(51) Int. Cl.
G02B 6/06 (2006.01)
A61B 1/06 (2006.01)
(52) U.S. Cl. .................. 385/118; 385/902; 600/182
(58) Field of Classification Search ........... 600/182, 600/175–177; 385/115–119, 902
See application file for complete search history.

(56) References Cited

U.S. PATENT DOCUMENTS 5,926,592 A    7/1999    Harris et al.
6,788,861 B1   9/2004    Utsui et al.
2006/0186325 A1  8/2006   Johnston et al.

FOREIGN PATENT DOCUMENTS

WO    2006/096155    9/2006

OTHER PUBLICATIONS

Barhoum et al., "Optical modeling of an ultrathin scanning fiber endoscope, a preliminary study of confocal versus non-confocal detection," Optics Express vol. 13, No. 19, pp. 7548-7562, Sep. 19, 2005.
U.S. Appl. No. 11/464,319 to Karasawa, filed Aug. 14, 2006.
U.S. Appl. No. 11/421,629 to Karasawa, filed Jun. 1, 2006.
U.S. Appl. No. 11/427,219 to Karasawa, filed Jun. 28, 2006.

*Primary Examiner*—Kevin S Wood
*Assistant Examiner*—John M Bedtelyon
(74) *Attorney, Agent, or Firm*—Greenblum & Bernstein, P.L.C.

(57) ABSTRACT

An endoscope has an optical fiber and at least one photo-detector. The optical fiber has a core that transmits illuminating light and at least one cladding that surrounds the core and transmits reflected light. The cladding has a refraction slope surface that is tapered toward a direction opposite the tip portion of the optical fiber. The photo-detector detects the reflected light that exits from the refraction slope surface by refraction.

23 Claims, 10 Drawing Sheets

ENDOSCOPE WITH OPTICAL FIBER AND FIBER OPTICS SYSTEM

BACKGROUND OF THE INVENTION

1. Field of the Invention

The present invention relates to an optical fiber which transmits light emitted from a light source, and further transmits light reflected off of an observed portion. In particular, it relates to a fiber-optics system used in observation equipment for acquiring information on an object.

2. Description of the Related Art

In a fiber-optics system, a single-mode optical fiber, which has a single core and an annular cladding surrounding the core, is utilized to transmit signals to a remote location. The single mode-optical fiber can be used to acquire image information on an object. The core is used for transmitting illuminating light, and the cladding is used for transmitting reflected light. In a double cladding optical fiber, light emitted from a light source passes through the core and exits from the tip portion of the optical fiber. Light reflected off of an object enters into the cladding of the optical fiber and progresses in the opposite direction. The optical fiber can be separated into two fiber segments, between which a beam splitter is provided. Light passing through a core in one optical fiber segment directly enters into a core of the other optical fiber segment via the beam splitter. The reflected light passing through the cladding of the other optical fiber is deflected by the beam splitter, and is directed to a photo-detector, such as a photodiode. The above fiber-optics system can be used in observation equipment, such as an endoscope or probe with a scanning optical fiber, a scanning microscope, and other similar observation systems, including confocal systems.

In the endoscope with a scanning optical fiber, a single-mode optical fiber is provided in the endoscope. The tip portion of the optical fiber is attached to a piezoelectric 2-D actuator such that the tip portion becomes a cantilever beam. The piezoelectric actuator two-dimensionally vibrates the cantilevered tip portion at a resonant frequency while modulating or amplifying amplitudes of the vibration, so that the tip portion of the optical fiber is driven in a spiral pattern. Light emitted from a light source, such as a laser, passes through a core of the optical fiber, and light exiting from the optical fiber is directed to an observed portion. Light reflected off of the observed portion enters into and passes through the cladding of the optical fiber. A photodiode provided in a processor, which is connected to the endoscope, detects the transmitted light.

A part of the reflected light penetrates through the cladding while the reflected light progresses. Consequently, the intensity of the reflected light can not be precisely detected by the photo-detector. On the other hand, in the case of a fiber-optics system with a beam splitter, a part of the light passing through the beam splitter may accidentally or erroneously enter into the cladding due to misalignment of the beam-splitter. Such misalignment may occur due to a change of a temperature or a vibration of the optical fiber. The light which accidentally passes through the cladding toward the tip portion is irradiated toward the observed portion, so that a beam spot on the observed portion is formed by light from the core and light from the cladding. This may result in enlargement of the beam spot.

SUMMARY OF THE INVENTION

An object of the present invention is to provide an endoscope with an optical fiber and a fiber-optic system that is utilized to acquire information on an object by a simple construction. Another object of the present invention is to provide a fiber-optics system that is capable of detecting light by a simple construction. Another object of the present invention is to provide a fiber-optics system that eliminates light that has erroneously entered in a cladding while transmitting light.

According to one aspect of the present invention, there is provided an endoscope including an optical fiber and at least one photo-detector. The optical fiber has a core and at least one cladding, and extends to a tip portion of the optical fiber. The core transmits illuminating light. The cladding surrounds the core and transmits reflected light. The photo-detector detects the reflected light. In the optical fiber, the cladding has a slope surface (herein, called "refraction slope surface"). The refraction slope surface is tapered toward the direction opposite the tip portion of the optical fiber. The reflected light passing through the cladding exits from the slope surface by refraction. The photo-detector detects the reflected light that exits from the refraction slope surface.

According to another aspect of the present invention, there is provided an endoscope tip portion including an actuator and at least one photo-detector. The actuator vibrates a tip portion of an optical fiber so as to scan illuminating light, exiting from the fiber tip portion, over an observed portion. The optical fiber has a core that transmits the illuminating light and has at least one cladding that surrounds the core and transmits reflected light. The photo-detector detects the reflected light. The cladding has a refraction slope surface that is tapered toward the direction opposite the tip portion of the optical fiber. The photo-detector detects the reflected light that exits from the refraction slope surface.

According to another aspect of the present invention, there is provided an endoscope system including a light source that emits illuminating light; an optical fiber that has a core that transmits the illuminating light and at least one cladding that surrounds the core and transmits reflected light; and at least one photo-detector that detects the reflected light. The cladding has a refraction slope surface that is tapered toward the direction opposite the tip portion of the optical fiber. The photo-detector detects the reflected light that exits from the refraction slope surface.

According to another aspect of the present invention, there is provided a fiber optics system including a light source that emits illuminating light; an optical fiber that has a core that transmits the illuminating light toward one tip portion of the optical fiber and that has at least one cladding that surrounds the core and that transmits reflected light; and a light detecting unit that has at least one photo-detector that detects the reflected light. The cladding has a refraction slope surface that is formed in the light detecting unit and that is tapered toward an opposite tip portion of the optical fiber. The photo-detector detects the reflected light that exits from the refraction slope surface.

According to another aspect of the present invention, there is provided a light-detecting unit including a housing that surrounds an optical fiber, and at least one photo-detector that detects reflected light. The optical fiber includes a core that transmits illuminating light toward one tip portion of the optical fiber and at least one cladding that surrounds the core and transmits reflected light. The cladding includes a refraction slope surface provided in the housing. The refraction slope surface is tapered toward an opposite tip portion of the optical fiber. The photo-detector detects reflected light that exits from the refraction slope surface.

According to another aspect of the present invention, there is provided an endoscope including an optical fiber that has a core that transmits illuminating light and that has at least one cladding that surrounds the core and that transmits reflected light; and at least one photo-detector that detects the reflected light. The cladding has a slope surface (hereinafter, called "attenuation slope surface") that is tapered toward the fiber tip portion. A part of the illuminating light that progresses in the cladding toward the fiber tip portion exits from the attenuation slope surface.

According to another aspect of the present invention, there is provided an endoscope tip portion including an actuator that vibrates a tip portion of an optical fiber so as to scan illuminating light exiting from the tip portion over an observed portion, and at least one photo-detector that detects the reflected light. The optical fiber has a core that transmits the illuminating light and that has at least one cladding that surrounds the core and that transmits reflected light. The cladding has an attenuation slope surface that is tapered toward the fiber tip portion. A part of the illuminating light that progresses in the cladding toward the fiber tip portion exits from the attenuation slope surface.

According to another aspect of the present invention, there is provided an endoscope system having a light source that emits illuminating light; an optical fiber that has a core that transmits the illuminating light and at least one cladding that surrounds the core and that transmits reflected light; and at least one photo-detector that detects the reflected light. The cladding has an attenuation slope surface that is tapered toward the fiber tip portion. A part of the illuminating light that progresses in the cladding toward the fiber tip portion exits from the attenuation slope surface.

According to another aspect of the present invention, there is provided a fiber optics system having a light source that emits illuminating light; and an optical fiber that has a core that transmits illuminating light and that has at least one cladding that surrounds the core and that transmits reflected light. The cladding has an attenuation slope surface that is tapered toward the fiber tip portion. A part of the illuminating light that progresses in the cladding toward the fiber tip portion exits from the attenuation slope surface by refraction.

According to another aspect of the present invention, there is provided a light-attenuation unit including an optical fiber having a core that transmits illuminating light toward a tip portion of the optical fiber and at least one cladding that surrounds the core and transmits reflected light; and a housing that surrounds said optical fiber. The cladding has an attenuation slope surface provided in the housing, the attenuation slope surface being tapered toward the tip portion of the optical fiber. Light that is emitted from a light source and that progresses in the cladding exiting from the attenuation slope surface.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein.

DESCRIPTION OF THE PREFERRED EMBODIMENTS

The present invention will be described below with reference to the embodiments shown in the drawings.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
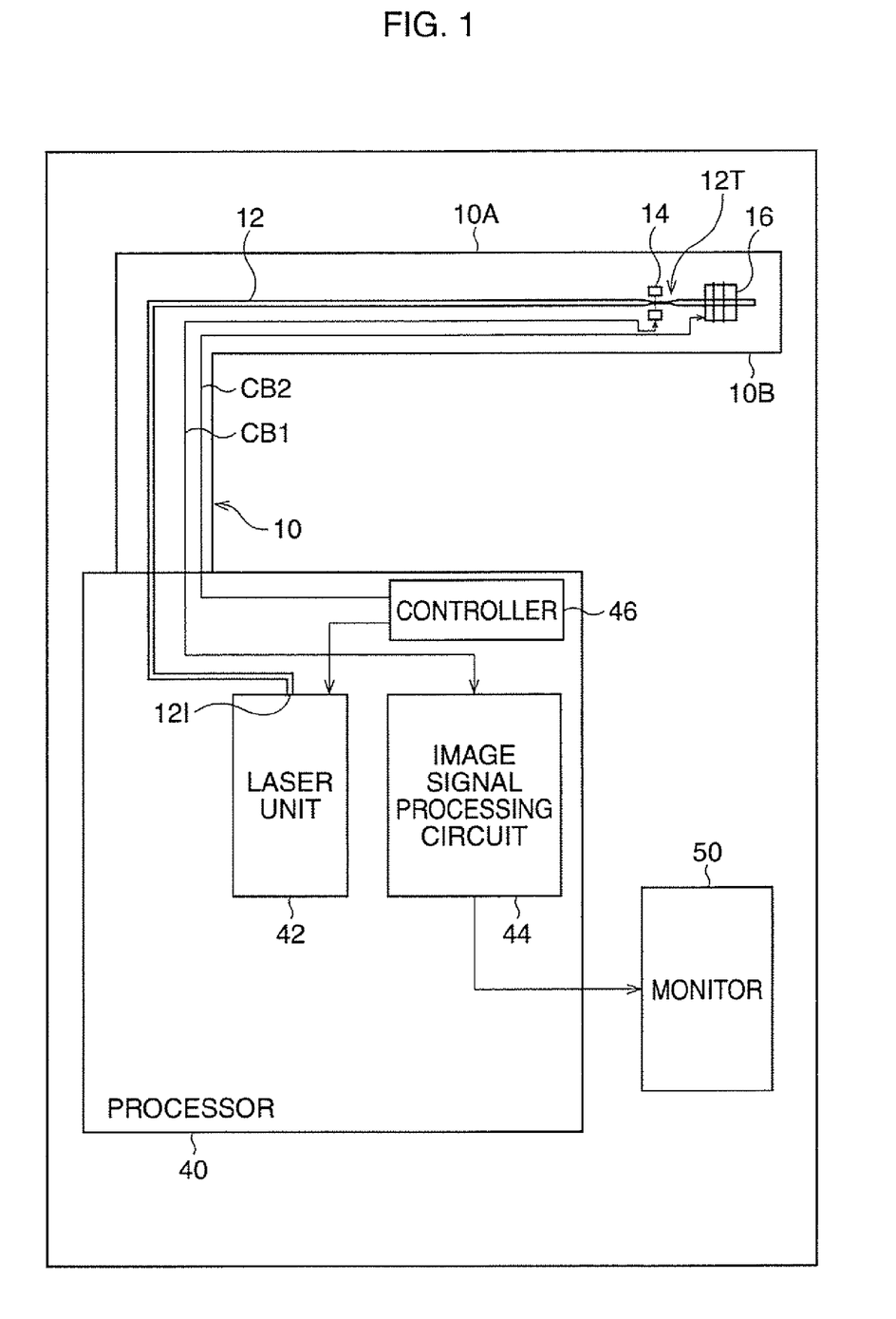
FIG. 1 is a block diagram of an endoscope system according to a first embodiment.

FIG. 1 is a block diagram of an endoscope system according to a first embodiment.

The endoscope system has an endoscope 10, a processor 40, and a monitor 50. The endoscope 10 is detachably connected to the processor 40, and a tubular and flexible insertion portion 10A is inserted into a body cavity. The monitor 50 is connected to the processor 40.

A laser unit 42, provided in the processor 40, emits a laser beam, and irradiated light enters an incident surface 12I of an optical fiber 12. The optical fiber 12 may be of any suitable type, such as a single-mode optical fiber. The optical fiber 12 extends through the endoscope 10 to the tip portion 10B of the endoscope 10 to direct the light from the proximal end to the distal end of the endoscope 10. The light passes through a core in the optical fiber 12, and exits from the tip portion 10B so that an observed portion is illuminated.

Light reflected off of the observed portion enters in a cladding of the optical fiber 12. The reflected light passes through the cladding, and exits from a light-refracting portion 12T of the optical fiber 12, as described later. A plurality of photodiodes 14, which is provided adjacent to the light-refracting portion 12T, detects the light exiting from the light-refracting portion 12T, and generates image-pixel signals. The generated image-pixel signals are successively read from the photodiodes 14 to an image signal processing circuit 44 in the processor 40 via a signal cable CB1. In the image signal processing circuit 44, the image-pixel signals are subjected to various processes to generate image signals. The generated image signals are fed to the monitor 50 so that a color-image is displayed on the monitor 50.

A controller 46 outputs control signals to the distal end of the endoscope 10 via a signal cable CB2 to control a piezoelectric actuator 16. A timing controller (not shown) outputs clock pulse signals to a photodiode driver (not shown), so as to synchronize a read-timing of the image-pixel signals with the driving of the actuator 16.

Figure 2:
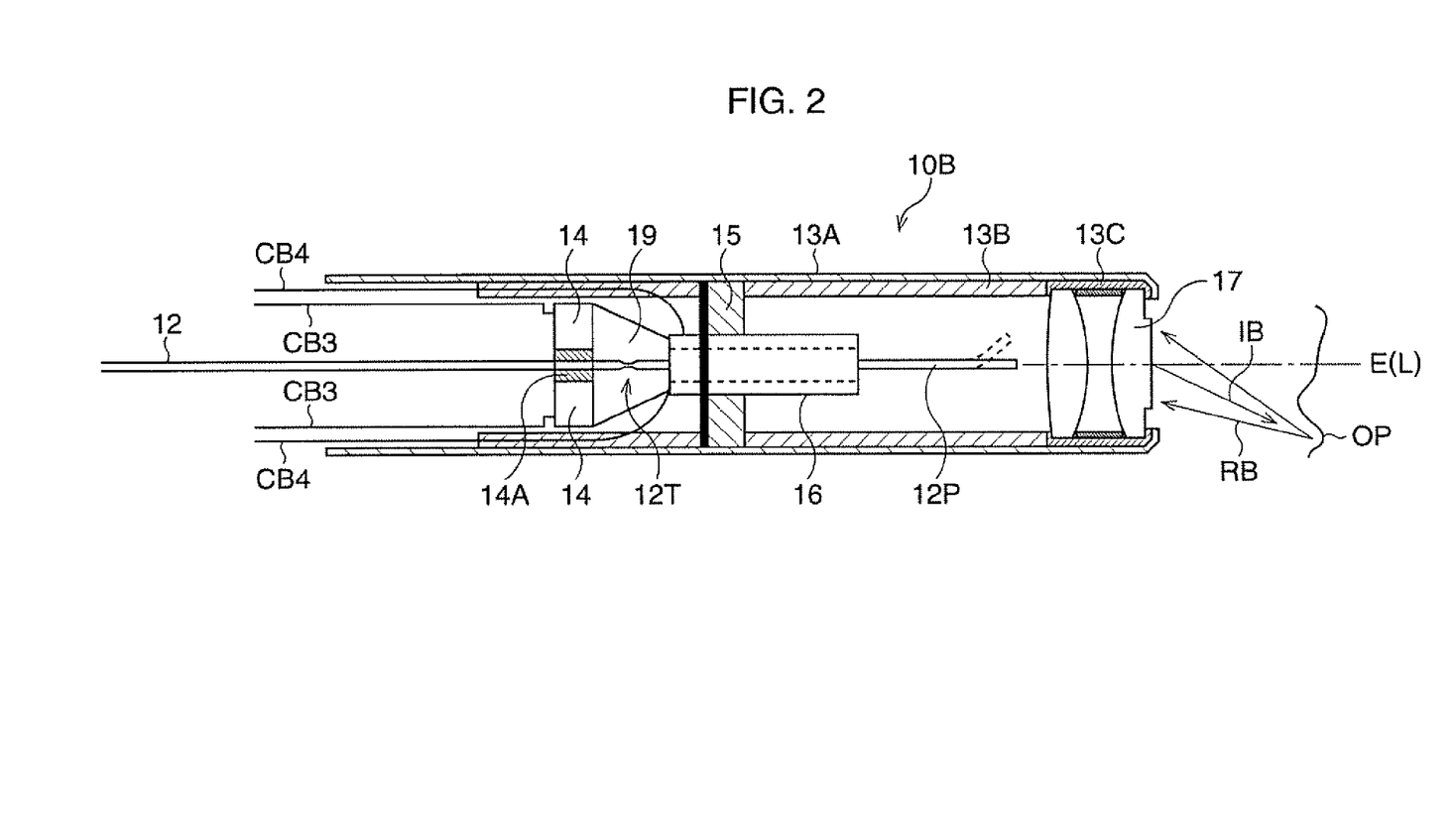
FIG. 2 is a view showing an inner construction of a tip portion of the endoscope.

FIG. 2 is a view showing an inner construction of the tip portion 10B of the endoscope 10.

In the tip portion 10B of the endoscope 10, an outer tube 13A is attached to the distal end of the insertion portion 10A shown in FIG. 1. An inner tube 13B, which is coaxially set in the outer tube 13A, accommodates or covers the tip portion 12P of the optical fiber 12. A ring-shaped holding member 13C, attached to the inner tube 13B, holds an optical system 17. The tubular piezoelectric actuator 16 is fastened coaxially to the inner tube 13B by a ring-shaped holding member 15, which is fixed to the inner tube 13B.

The optical fiber 12 passes through along the longitudinal axis L of the inner tube 13B; namely, the tip portion 10B, and projects from the actuator 16. The optical system 17, including an objective lens, is disposed at the tip portion 10B, and directs or refracts the light from the tip portion 12P of the optical fiber 12. The optical axis E of the optical system 17 coincides with the longitudinal axis L.

The vibrating optical fiber 12 projects from the actuator 16 along the axis L so that the tip portion 12P of the optical fiber 12 becomes a cantilever. An adhesive (not shown) is applied to the end portion of the actuator 16 to hold the cantilevered tip portion 12P securely. The tube-shaped bimorph-type piezoelectric actuator 16 is composed of piezoelectric materials, such as PZT.

The piezoelectric actuator 16 deforms by the inverse piezoelectric effect, and two-dimensionally drives the tip portion 12P so as to resonate the tip portion 12P. Namely, the piezoelectric actuator 16 vibrates the tip portion 12P along two axes perpendicular to each other while modulating or amplifying amplitudes of the vibration, so as to move the end surface of the tip portion 12P in a spiral. Herein, the tip portion 12P vibrates in a first resonant mode. The actuator 16 is connected to cables CB4, which are connected to the cable CB2 shown in FIG. 1.

The optical system 17 refracts the light from the optical fiber 12 so as to radiate the light IB from a center point of the optical system 17 toward the observed portion OP. Thus, the observed portion OP is irradiated. The tip portion 12P of the optical fiber 12 is repeatedly driven spirally in each frame time-interval. The plurality of photodiodes 14, disposed around the optical fiber 12, is arrayed circumferentially at given constant intervals, and attached to a sleeve 14A, through which the optical fiber 12 passes. The photodiodes 14 are connected to connecting cables CB3, which are connected to the signal cable CB1 shown in FIG. 1.

Figure 3:
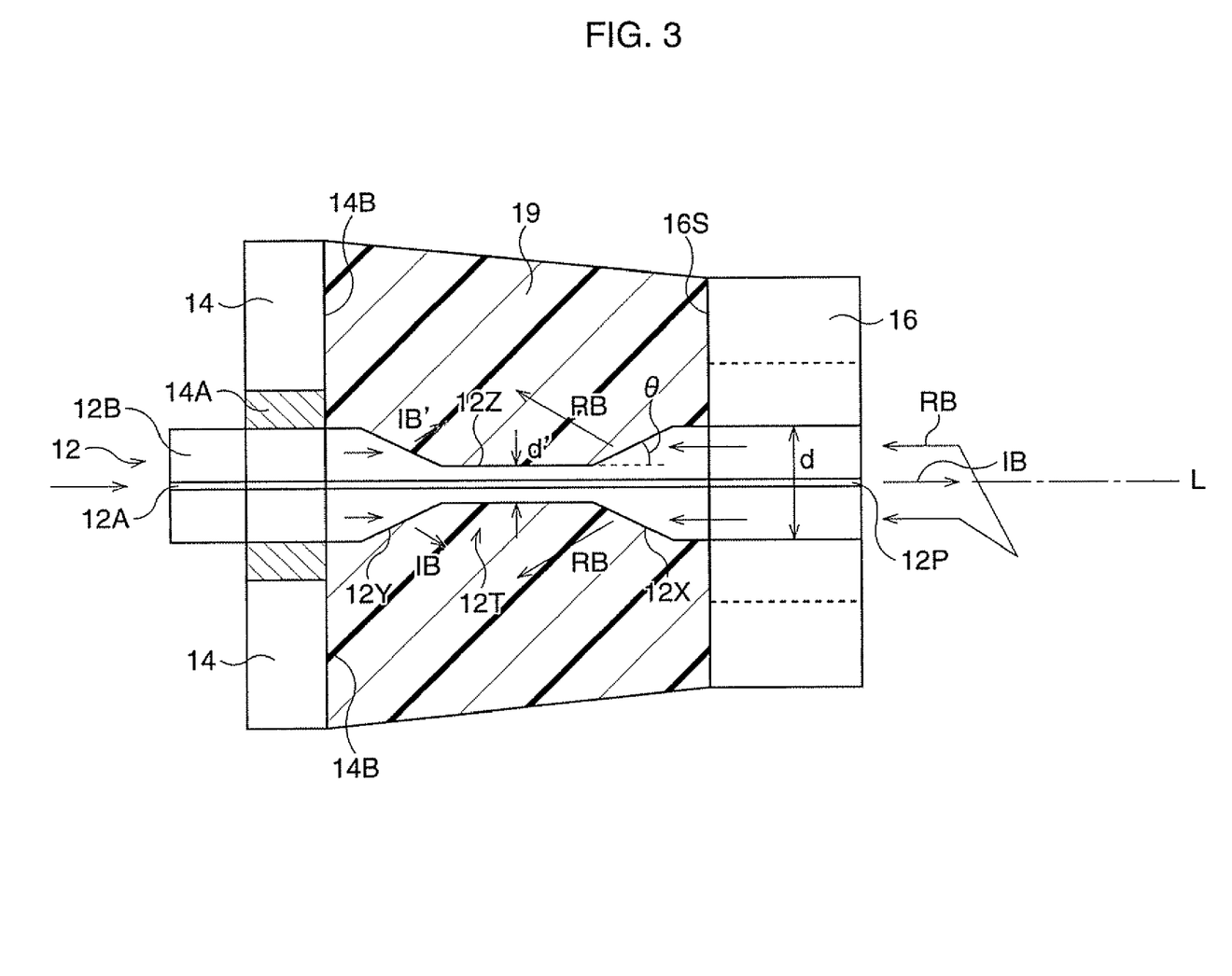
FIG. 3 is a view showing a light-refracting portion of an optical fiber.

FIG. 3 is a view showing the light-refracting portion 12T of the optical fiber 12.

In the optical fiber 12, the doped core 12A, which may be made of any suitable material, extends along the center axis of the optical fiber 12. The optical fiber also includes a cladding 12B which extends along the center axis of the optical fiber 12 and surrounds the core 12A. The cladding 12B may be made of any suitable material, such as glass. Further, the optical fiber 12 in the first embodiment is a single-cladding optical fiber. In the light-refracting portion 12T, a slope surface 12X is formed on the outer surface of the cladding 12B or optical fiber 12. The slope surface 12X is tapered toward a direction opposite the tip portion 12P, and symmetrical to the longitudinal direction or the center axis of the optical fiber 12. The configuration of the optical fiber 12 corresponding to the slope surface 12X is formed in a cone, and therefore the slope angle "θ" is substantially constant. Further, a cone-shaped slope surface 12Y, which is tapered toward the tip portion 10B of the endoscope 10, is formed on the cladding 12B. The slope surface 12X and the slope surface 12Y are opposite each other with a thin portion 12Z of the optical fiber 12 intervening. The diameter "d'" of the thin portion 12Z is smaller than the diameter "d" of the other portion of the optical fiber 12. The light-refracting portion 12T may be formed in any suitable manner, such as by etching the cladding 12B so as to reduce the diameter "d'".

The sleeve-shaped resin 19 is disposed between the photo-detectors 14 and the actuator 16 so as to tightly contact the end surface 16S of the actuator 16 and a photo-receiving area 14B of each photo-detector 14. The resin 19 may be made of any suitable material, such as polymethyl methacrylate (PMMA). The resin has a refractive index higher or greater than that of the cladding 12B. Consequently, the reflected light RB, passing through the cladding 12B, is refracted by the slope surface 12X, which is a boundary surface between the cladding 12B and the resin 19. The reflected light RB exiting from the slope surface 12X progresses toward the photo-detectors 14. The slope angle "θ" of the slope surface 12X relative to the longitudinal direction L is determined in accordance with the refractive index of the resin 19, the refractive index of the cladding 12B, and the position of the photo-detectors 14.

As shown in FIG. 3, part of the light that is emitted from the laser unit 42 may accidentally or erroneously enter into the cladding 12B. This may occur for various reasons, such as due to a misalignment between the incident surface 12I of the optical fiber 12 and the laser unit 42. The entered light, passing through the cladding 12B, is refracted by the slope surface 12Y so that the light IB' in the cladding 12B exits from the slope surface 12Y. This prevents such undesirable excess light from reaching the observed portion.

The photodiodes 14 convert the detected light into signals. The generated image-pixel signals are then read from the photo-detectors 14 in a time-series, and are then fed to the image signal processing circuit 44 shown in FIG. 1. R, G, and B color filters are respectively disposed on the photodiodes 14 such that the ratio of the colors R, G, and B is usually equal. In the image signal processing circuit 44, color in each pixel is detected from signals fed from the plurality of photo-detectors 14. For example, when the ratio of signals fed from photodiodes with an R filter is larger than that fed from photodiodes with the other (G, B) filters, the pixel color is set to a reddish color.

In this manner, in the first embodiment, the light-refracting portion 12T is formed at a portion of the optical fiber 12 in which the slanted surfaces 12X and 12Y are formed on the cladding 12B. The resin 19 having the relatively high refractive index covers the light-refracting portion 12T. The reflected light RB is refracted on the slope surface 12X so that the reflected light exits from the cladding 12B and enters into the photodiodes 14. Thus, the reflected light is fully collected without attenuation of the reflected light and is detected precisely.

Figure 4:
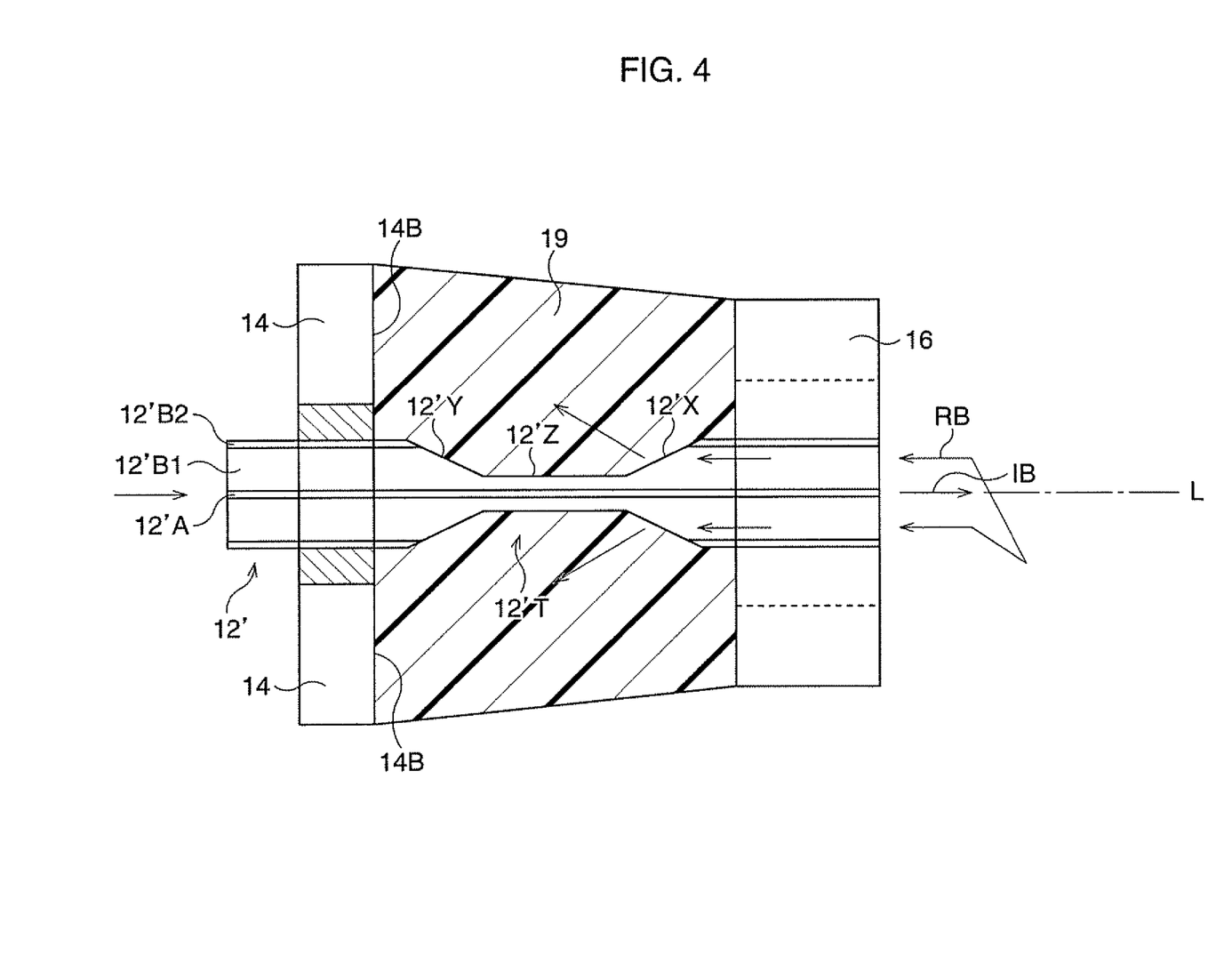
FIG. 4 is a view showing a light-refracting portion of an optical fiber according to a second embodiment.

FIG. 4 is a view showing a light-refracting portion of an optical fiber according to a second embodiment. The second embodiment is different from the first embodiment in that a double-cladding optical fiber is used. Other elements of the second embodiment are substantially the same as those of the first embodiment.

As shown in FIG. 4, a single-mode optical fiber 12', which has core 12'A and double claddings composed of an inner cladding 12'B1 and an outer cladding 12'B2, extends along the longitudinal direction L. In the light-refracting portion 12'T, a slope surface 12'X is formed on the outer surface of the outer cladding 12'B2, and a slope surface 12'Y is formed so as to be opposite the slope surface 12'X. In this manner a thin portion 12'Z is formed in the optical fiber 12'. The light-refracting portion 12'T is formed by etching the inner cladding 12'B1 and the outer cladding 12'B2.

Figure 5:
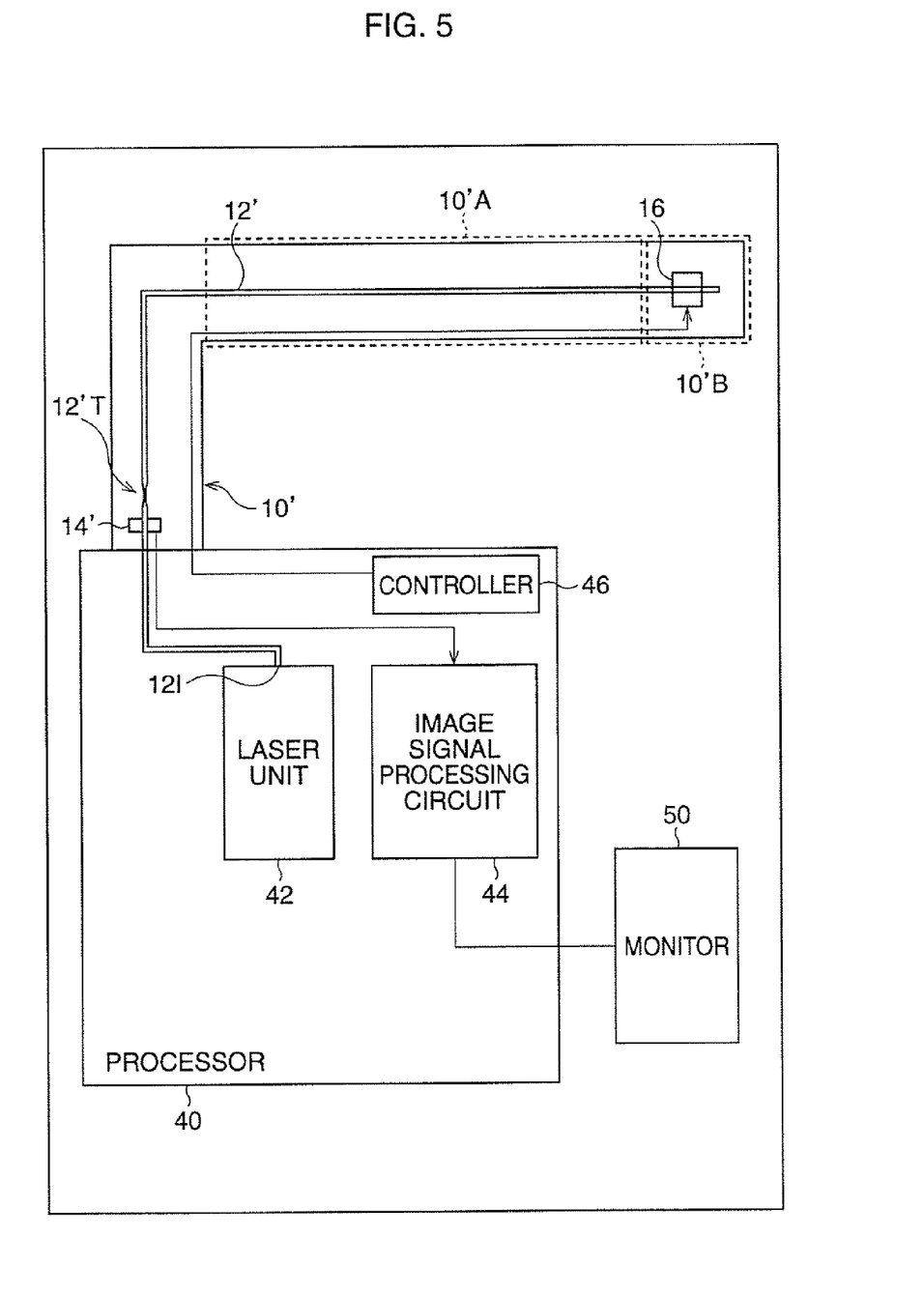
FIG. 5 is a block diagram of an endoscope system according to a third embodiment.

FIG. 5 is a block diagram of an endoscope system according to a third embodiment. The third embodiment is different from that first and the second embodiment in that a light-refracting portion is formed at the proximal end of an endoscope. Other elements of the third embodiment are substantially the same as those of the first and second embodiments.

In an endoscope 10', a single-mode, double-cladding optical fiber 12' extends through an endoscope 10', and a light-refracting portion 12'T is formed at the proximal end of the endoscope 10'. Photo-detectors 14' are disposed adjacent to the light-refracting portion 12'T. A resin is disposed laterally to the light-refracting portion 12'T, similar to the first and second embodiments. Since the double-cladding optical fiber 12' is effective for attenuation of light, the reflected light is directly detected by the photodiodes 14', and adequate image signals are generated.

Figure 6:
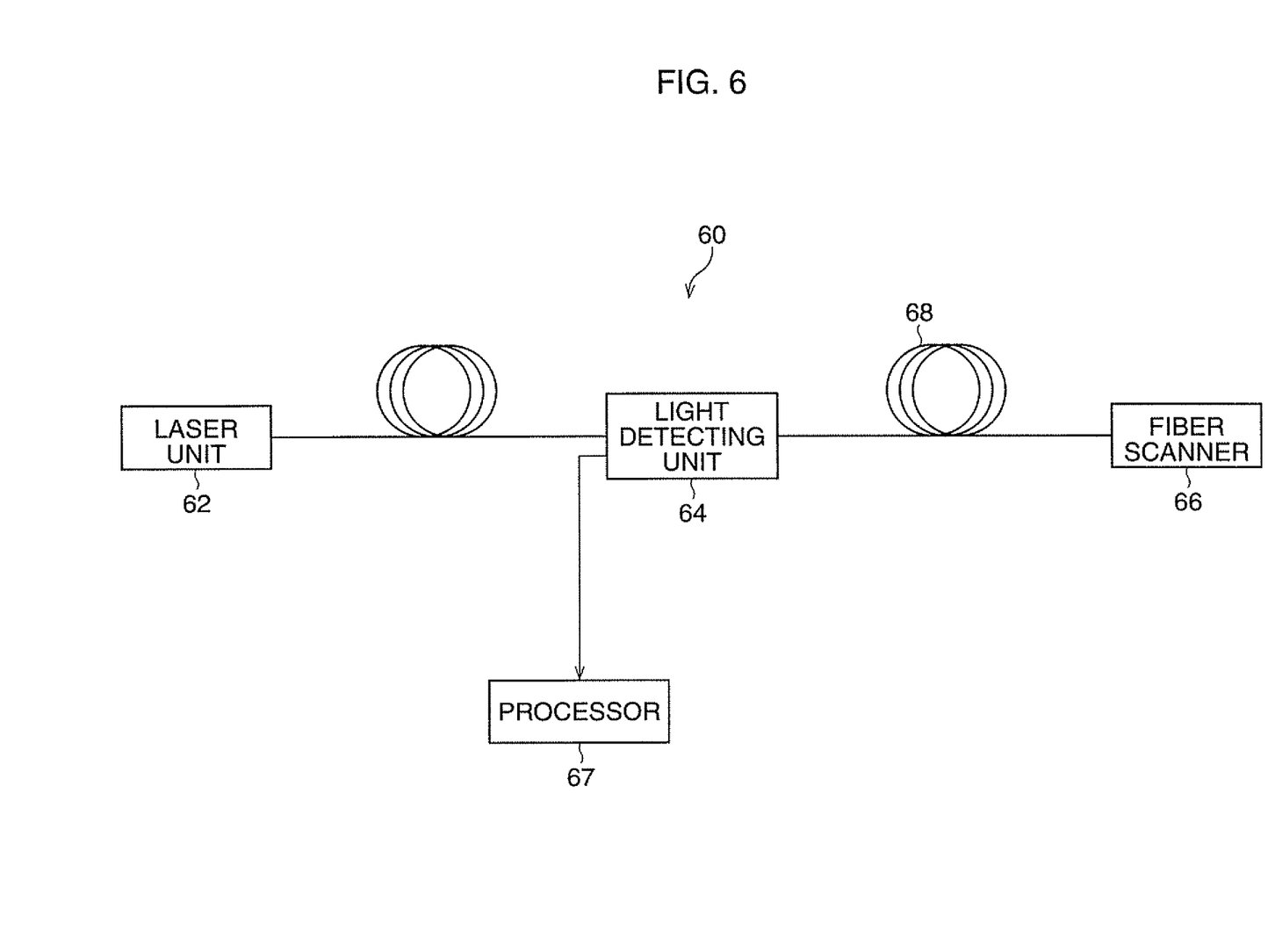
FIG. 6 is a view showing a fiber-optics system according to a fourth embodiment.

FIG. 6 is a view showing a fiber-optics system according to a fourth embodiment, which is used for observing an object.

A fiber-optics system 60 is equipped with a laser unit 62, a light-detecting unit 64, and a fiber scanner 66, through which a single-mode and double-cladding optical fiber 68 passes. Light emitted from the laser unit 62 passes through the optical fiber 68 and is transmitted to the fiber scanner 66. In the fiber scanner 66, similarly to with the first embodiment, the tip portion of the optical fiber 68 is driven spirally so that the observed portion is illuminated. Reflected light passes through the optical fiber 68 and reaches the light-detecting unit 64. In the light-detecting unit 64, the reflected light is converted to image signals, and is transmitted to a processor 67. In the processor 67, the video signals are generated on the basis of the image signals.

Figure 7:
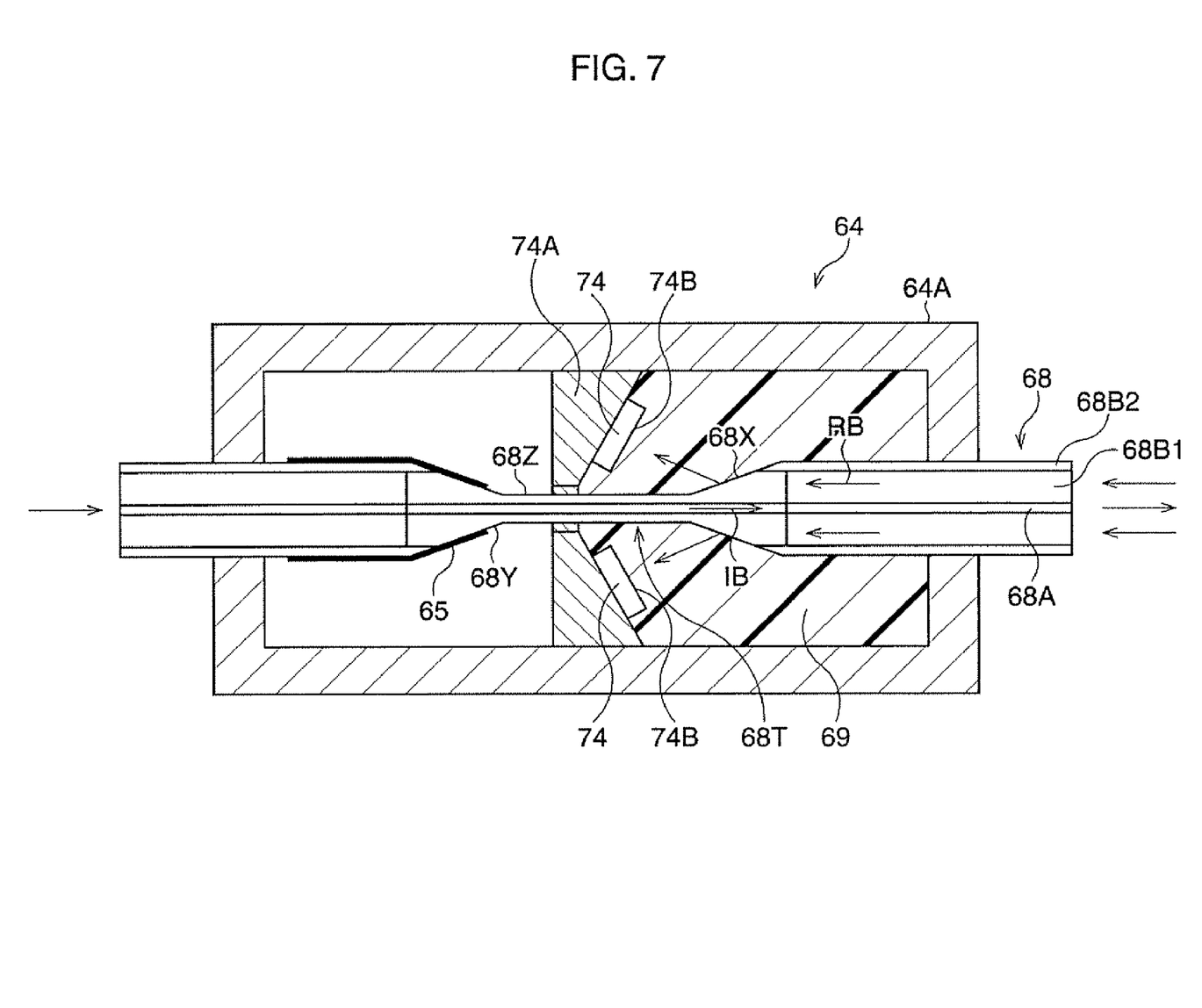
FIG. 7 is a view showing an inner construction of a light detecting unit.

FIG. 7 is a view showing an inner construction of the light-detecting unit 64 of the fourth embodiment. The optical fiber 68 has a core 68A and double claddings composed of an inner cladding 68B1 and an outer cladding 68B2. The optical fiber 68 has a light-refracting portion 68T, in which a slope surface 68X and a slope surface 68Y are formed. In this manner a thin portion 68Z is formed in the optical fiber 68. Photodiodes 74 are disposed around the light-refracting portion, and are supported by a supporting member 74A, such that a photo-receiving area 74B of each photodiode 74 faces the slope surface 68X. A resin 69, such as PMMA, is loaded in an inner space formed by a housing 64A and the supporting member 74A. A shield member 65, which blocks light, covers the slope surface 68Y.

Figure 8:
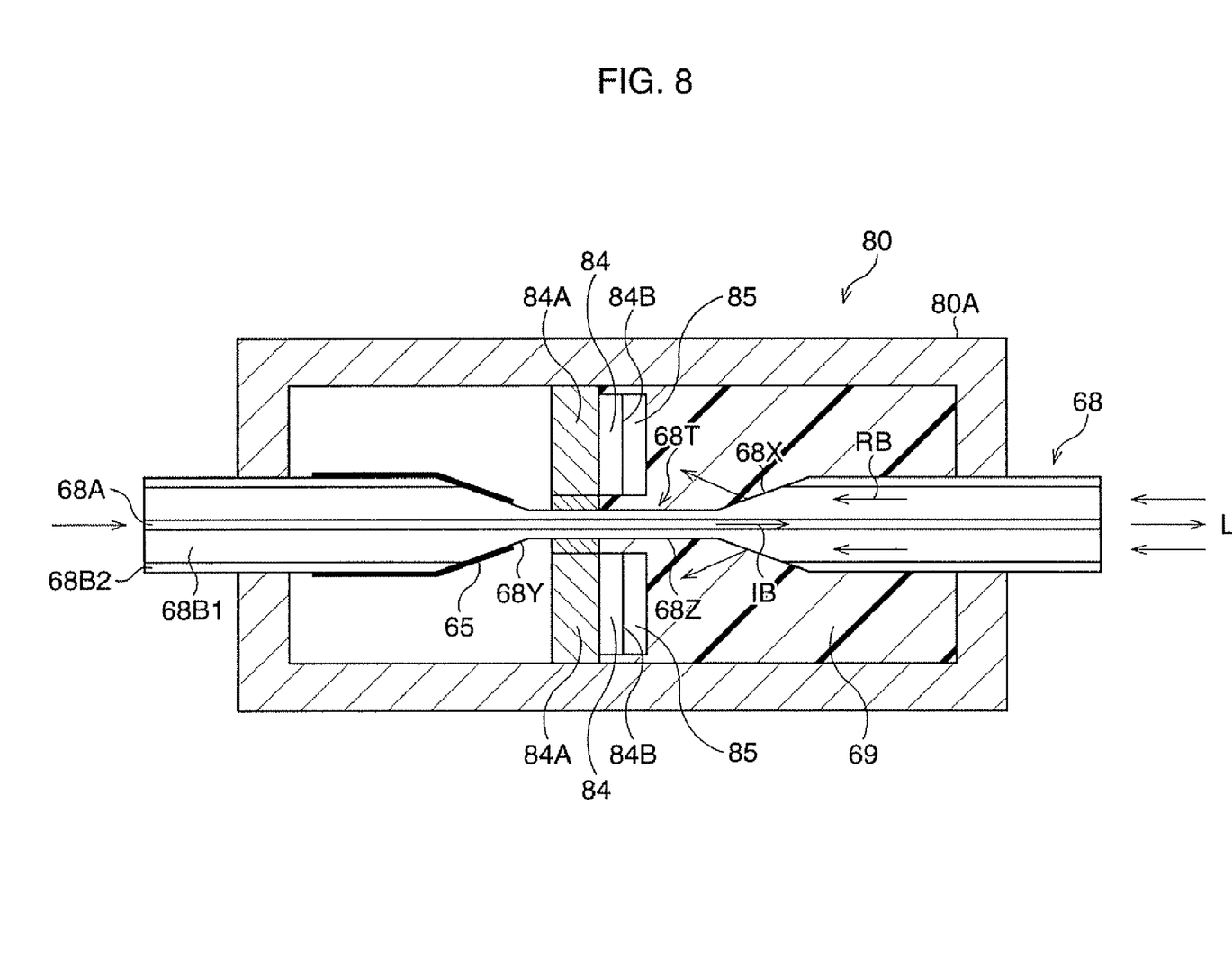
FIG. 8 is a view showing an inner construction of a light detecting unit according to a fifth embodiment.

FIG. 8 is a view showing an inner construction of a light detecting unit according to a fifth embodiment. The fifth embodiment is different from the fourth embodiment in that a glass lens is provided. Other elements of the fifth embodiment are substantially the same as those of the fourth embodiment.

A light-detecting unit 80 includes a housing 80A in which a plurality of photodiodes 84 are disposed around the light-refracting portion 68T, and are supported by a supporting member 84A such that a photo-receiving area 84B of each photodiode 84 faces a direction along a longitudinal direction of the optical fiber 68. A plurality of glass lenses 85 is disposed in front of the plurality of photodiodes 84. Each glass lenses refracts light passing through the slope surface 68X to the photo-receiving area 84B.

Figure 9:
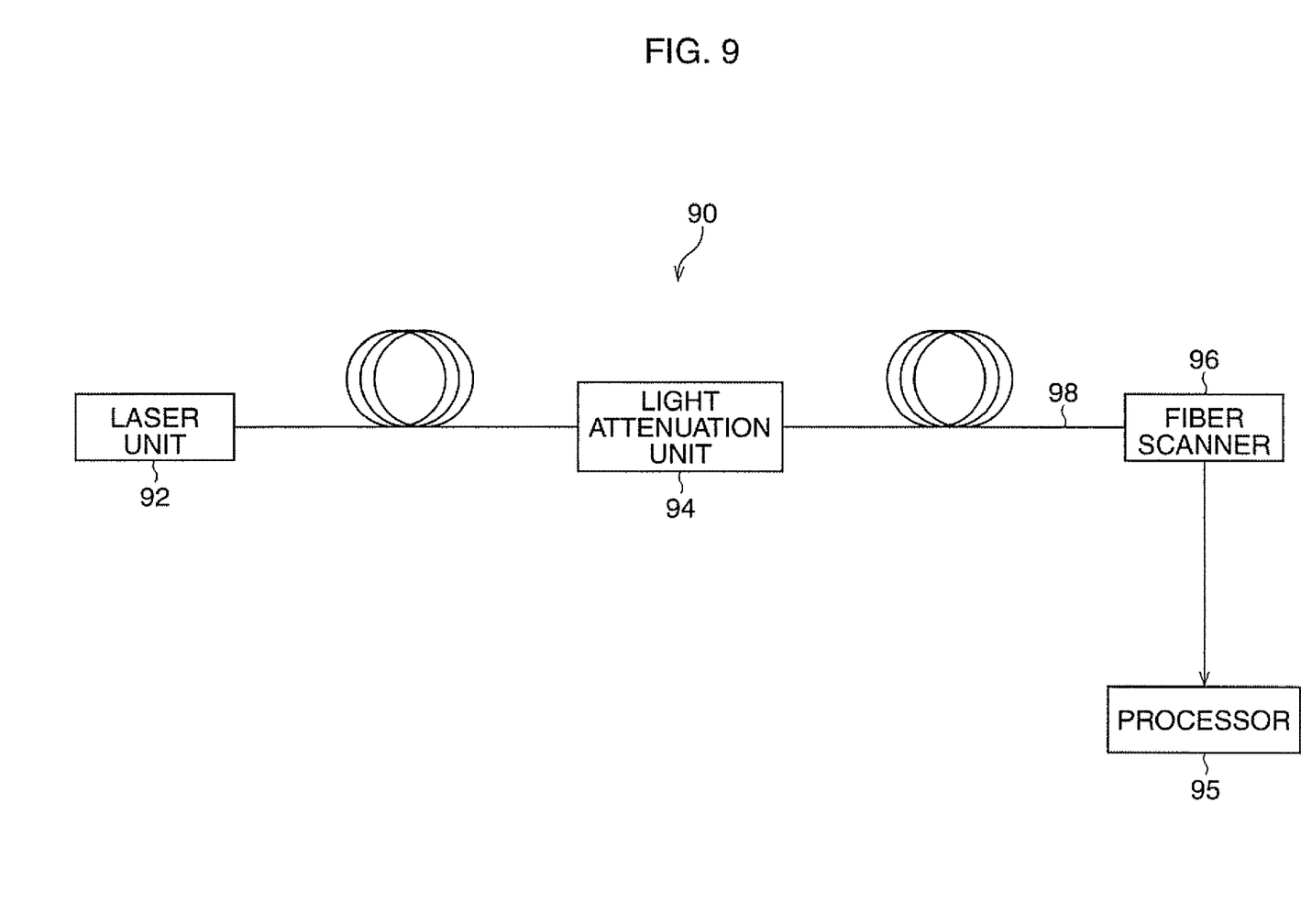
FIG. 9 is a view showing a fiber optics system according to a sixth embodiment.

FIG. 9 is a view showing a fiber optics system according to a sixth embodiment. In the six embodiment, a light attenuation unit is used.

A fiber-optics system 90 is equipped with a laser unit 92, a light attenuation unit 94, and a fiber scanner 96, through which a single-mode and double-cladding optical fiber 98 passes. Light reflected off an observed portion is converted to image-pixel signals by photo-detectors provided in a fiber scanner 96, and is transmitted to a processor 95.

Figure 10:
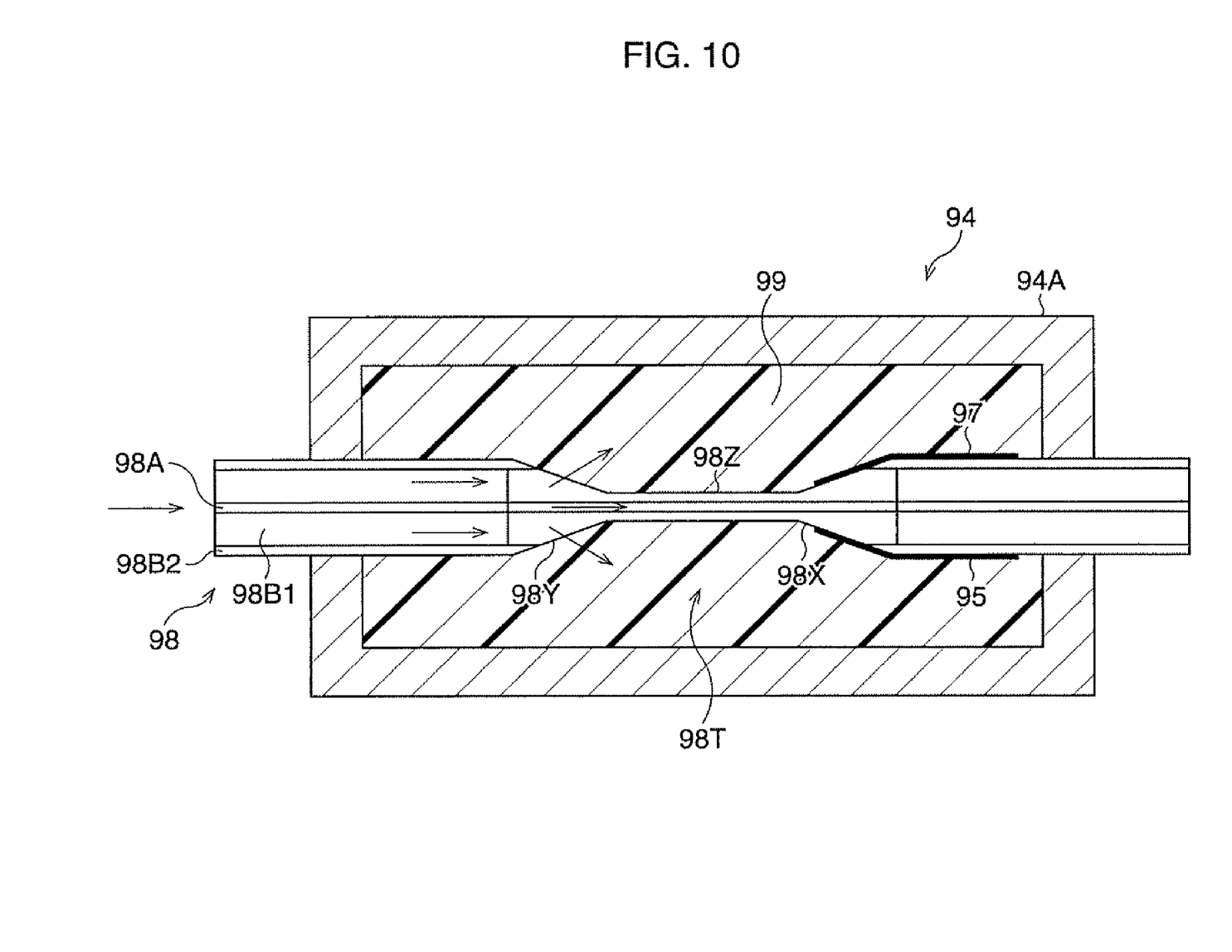
FIG. 10 is a view showing an inner construction of a light attenuation unit.

FIG. 10 is a view showing an inner construction of the light attenuation unit 94 of the sixth embodiment.

In the light attenuation unit 94, a resin 99 is loaded into a housing 94A. The optical fiber 98 has a core 98A and double claddings composed of an inner cladding 98B1 and an outer cladding 98B2. The optical fiber 98 has a light-refracting portion 98T, in which slope surfaces 98X and 98Y, and a thin portion 98Z are formed. A shield member 95 covers the slope surface 98X to block light entering into the optical fiber 98. Light progressing through the cladding 98B1 is refracted by the slope surface 98Y so that the light exits from the cladding 98B1 along the slope surface 98Y. Consequently, light erroneously or accidentally entered in the cladding 98B1 exits from the optical fiber 98, and does not reach the observed area.

Optionally, another suitable resin having a relatively high refractive index can be used instead of PMMA. The reflected or illuminating light may be refracted without a resin. In this case, the slope angle of the slope surface is determined in accordance with Snell's law of refraction, such that an incidence angle does not exceed a critical angle.

Finally, it will be understood by those skilled in the arts that the foregoing description is of preferred embodiments of the device, and that various changes and modifications may be made to the present invention without departing from the spirit and scope thereof.

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

Although the invention has been described with reference to several exemplary embodiments, it is understood that the words that have been used are words of description and illustration, rather than words of limitation. As the present invention may be embodied in several forms without departing from the spirit or essential characteristics thereof it should also be understood that the above-described embodiments are not limited by any of the details of the foregoing description, unless otherwise specified. Rather, the above-described embodiments should be construed broadly within the spirit and scope of the present invention as defined in the appended claims. Therefore, changes may be made within the metes and bounds of the appended claims, as presently stated and as amended, without departing from the scope and spirit of the invention in its aspects.

What is claimed is:

1. An endoscope, comprising:
   an optical fiber having a core that transmits illuminating light and at least one cladding that surrounds the core, the cladding transmitting reflected light;
   at least one photo-detector that detects the reflected light, the cladding comprising a refraction slope surface that is tapered toward a direction of a proximal end of the optical fiber, the photo-detector detecting reflected light that exits from the refraction slope surface; and
   an actuator that vibrates a tip portion of the optical fiber so as to scan the illuminating light over an observed portion, the tip portion being defined at a front end of the endoscope, and
   the refraction slope surface being formed at a portion of the optical fiber so as to be positioned rearward of the actuator with respect to the front end of the endoscope.

2. The endoscope according to claim 1, further comprising a resin surrounding the refraction slope surface, the resin having a refractive index higher than a refractive index of the cladding.

3. The endoscope according to claim 2, wherein the resin comprises polymethyl methacrylate (PMMA).

4. The endoscope according to claim 2, wherein the resin is transparent.

5. The endoscope according to claim 2, wherein the refractive index of the resin is defined such that the reflected light exiting from the refraction slope surface progresses toward the photo-detector.

6. The endoscope according to claim 1, wherein the optical fiber comprises a single-mode optical fiber.

7. The endoscope according to claim 1, wherein the optical fiber comprises a single-cladding optical fiber.

8. The endoscope according to claim 1, wherein the optical fiber comprises a double-cladding optical fiber.

9. The endoscope according to claim 1, wherein the actuator comprises a tubular piezoelectric actuator.

10. The endoscope according to claim 1, wherein the refraction slope surface is formed at a portion of the optical fiber adjacent to a proximal end of the endoscope.

11. The endoscope according to claim 1, wherein the photo-detector comprises a photodiode.

12. The endoscope according to claim 1, wherein the photo-detector is positioned such that a photo-receiving area of the photo-detector faces in a direction along a longitudinal axis of the optical fiber.

13. The endoscope according to claim 12, further comprising a glass lens that is positioned in front of the photo-receiving area and refracts the reflected light toward the photo-receiving area.

14. The endoscope according to claim 1, wherein the photo-detector is oriented at an angle relative to a longitudinal axis of the optical fiber so as to face the refraction slope surface.

15. The endoscope according to claim 1, wherein a plurality of photo-detectors are positioned laterally with respect to the optical fiber.

16. The endoscope according to claim 1, wherein an angle of the refraction slope surface relative to a longitudinal axis of optical fiber is defined such that the reflected light exiting from the refraction slope surface progresses toward the photo-detector.

17. The endoscope according to claim 1, wherein the refraction slope surface is positioned symmetrical with respect to a center axis of the optical fiber.

18. The endoscope according to claim 1, wherein the cladding further comprises an attenuation slope surface opposing the refraction slope surface.

19. The endoscope according to claim 18, further comprising a shield member that covers the attenuation slope surface.

20. The endoscope according to claim 1, wherein the refraction slope surface comprises a conical surface.

21. The endoscope according to claim 1, wherein the refraction slope surface is formed by etching the cladding.

22. An endoscope tip portion, comprising:
    an actuator that vibrates a tip portion of an optical fiber so as to scan illuminating light exiting from the tip portion over an observed portion, the tip portion being defined at a front end of the endoscope, the optical fiber having a core that transmits the illuminating light and at least one cladding that surrounds the core, and the cladding transmitting reflected light; and
    at least one photo-detector that detects the reflected light, the cladding comprises a refraction slope surface that is tapered toward a direction of a proximal end of the optical fiber, the photo-detector detecting reflected light that exits from the refraction slope surface, and the refraction slope surface being formed at a portion of the optical fiber so as to be positioned rearward of the actuator with respect to the front end of the endoscope.

23. An endoscope system, comprising:

a light source that emits illuminating light;

an optical fiber having a core that transmits the illuminating light and at least one cladding that surrounds the core, the cladding transmitting reflected light;

at least one photo-detector that detects the reflected light, wherein the cladding comprises a refraction slope surface that is tapered toward a direction of a proximal end of the optical fiber, the photo-detector detecting reflected light that exits from the refraction slope surface; and an actuator that vibrates a tip portion of the optical fiber so as to scan the illuminating light over an observed portion, the tip portion being defined at a front end of the endoscope, and the refraction slope surface being formed at a portion of the optical fiber so as to be positioned rearward of the actuator with respect to the front end of the endoscope.

* * * * *